United States Patent
Apfel

(10) Patent No.: US 8,831,244 B2
(45) Date of Patent: Sep. 9, 2014

(54) PORTABLE TONE GENERATOR FOR PRODUCING PRE-CALIBRATED TONES

(75) Inventor: Russell J. Apfel, Austin, TX (US)

(73) Assignee: Audiotoniq, Inc., Austin, TX (US)

( * ) Notice: Subject to any disclaimer, the term of this patent is extended or adjusted under 35 U.S.C. 154(b) by 649 days.

(21) Appl. No.: 13/104,955

(22) Filed: May 10, 2011

(65) Prior Publication Data

US 2012/0288119 A1   Nov. 15, 2012

(51) Int. Cl.
- H03G 5/00 (2006.01)
- H03G 3/30 (2006.01)
- A61B 5/12 (2006.01)
- H04R 25/00 (2006.01)

(52) U.S. Cl.
CPC .............. *A61B 5/123* (2013.01); *H03G 3/3089* (2013.01); *H04R 25/70* (2013.01)
USPC ................ 381/101; 381/58; 381/60; 381/312

(58) Field of Classification Search
USPC ................... 381/101–103, 98, 60, 77, 79, 56, 381/58–59, 312, 320; 700/94; 600/559
See application file for complete search history.

(56) References Cited

U.S. PATENT DOCUMENTS

| | | | |
|---|---|---|---|
| 5,197,332 A | 3/1993 | Shennib | |
| 6,350,243 B1 | 2/2002 | Johnson | |
| 6,366,863 B1 | 4/2002 | Bye et al. | |
| 6,468,224 B1 | 10/2002 | Foreman et al. | |
| 6,964,642 B2 | 11/2005 | Wasden et al. | |
| 6,974,421 B1 | 12/2005 | Causevic et al. | |
| 7,037,274 B2 | 5/2006 | Thornton et al. | |
| 7,370,533 B2 | 5/2008 | Davis | |
| 7,464,595 B2 | 12/2008 | Davis | |
| 2009/0279707 A1* | 11/2009 | Swartz | 381/58 |
| 2011/0301729 A1* | 12/2011 | Heiman et al. | 700/94 |

* cited by examiner

*Primary Examiner* — Vivian Chin
*Assistant Examiner* — Friederich W Fahnert
(74) *Attorney, Agent, or Firm* — Lee & Hayes, PLLC

(57) ABSTRACT

A portable tone generator includes a connector configurable to couple to an input/output port of a computing device, a memory configured to store data corresponding to a plurality of frequencies, and an output interface configurable to couple to a speaker system. The portable tone generator further includes tone generating circuitry coupled to the input interface, the output interface, and the memory. The tone generating circuitry is configured to receive a control signal from the computing device identifying a selected frequency of the plurality of frequencies, retrieve the data corresponding to the selected frequency, produce an output signal including a tone based on the data in response to receiving the control signal, and provide the output signal to the output interface.

20 Claims, 4 Drawing Sheets

PORTABLE TONE GENERATOR FOR PRODUCING PRE-CALIBRATED TONES

FIELD

This disclosure relates generally to a tone generator, and more particularly to a portable tone generator for producing pre-calibrated tones, which can be used for an at home hearing test.

BACKGROUND

Hearing deficiencies can range from partial to complete hearing loss. Often, an individual's hearing ability varies across the range of audible sound frequencies, and many individuals have hearing impairment with respect to only select acoustic frequencies. For example, an individual's hearing loss may be greater at higher frequencies than at lower frequencies.

Hearing aids have been developed to alleviate the effects of hearing losses in individuals. In instances where the individual's hearing loss varies across frequencies, such hearing aids can be tuned to compensate for the unique variations of the individual's hearing loss.

Typically, a hearing health professional performs a hearing test by taking measurements using calibrated and specialized equipment, such as an audiometer, to assess an individual's hearing capabilities in a variety of sound environments. The hearing test can include a variety of measurements, such as, an air conduction test, a bone conduction test, and a speech recognition test. The hearing health professional conduct the hearing test to produce an audiogram or a representation of an individual's hearing loss. Each audiogram includes a detailed report for one of the individual's ears.

Unfortunately, to take calibrated measurements to the level of accuracy required, the hearing health professional must purchase an audiometer system designed specifically with hearing tests in mind. Such systems have pre-calibrated system specific speakers, a bone conductor, an audio card, and audio samples (tone and speech samples). Such systems are often expensive, large, and sometimes difficult to operate. Computing devices, such as a personal computer, are not typically used because of the difficulties in consistently and reliably calibrating the wide range of hardware configurations of available computing devices.

BRIEF DESCRIPTION OF THE DRAWINGS

In the following description, the use of the same reference numerals in different drawings indicates similar or identical items.

DETAILED DESCRIPTION OF ILLUSTRATIVE EMBODIMENTS

Embodiments of a system for performing hearing tests on a computing device are described below that include a speaker system (such as a head set or bone conduction device) connected to a portable tone generator configured to interface with a computing device. In some embodiments, the portable tone generator includes software to produce a user interface on the computing device and hardware to produce (pre-calibrated, reliable audio signals for the speaker system independent of the computing device. In other embodiments, the portable tone generator is controlled by software executing on the computing device to produce the pre-calibrated, reliable audio signals for the speaker system. Calibration may be performed on the portable tone generator and associated speaker system during manufacturing and prior to shipment of the apparatus to an end user.

Figure 1:
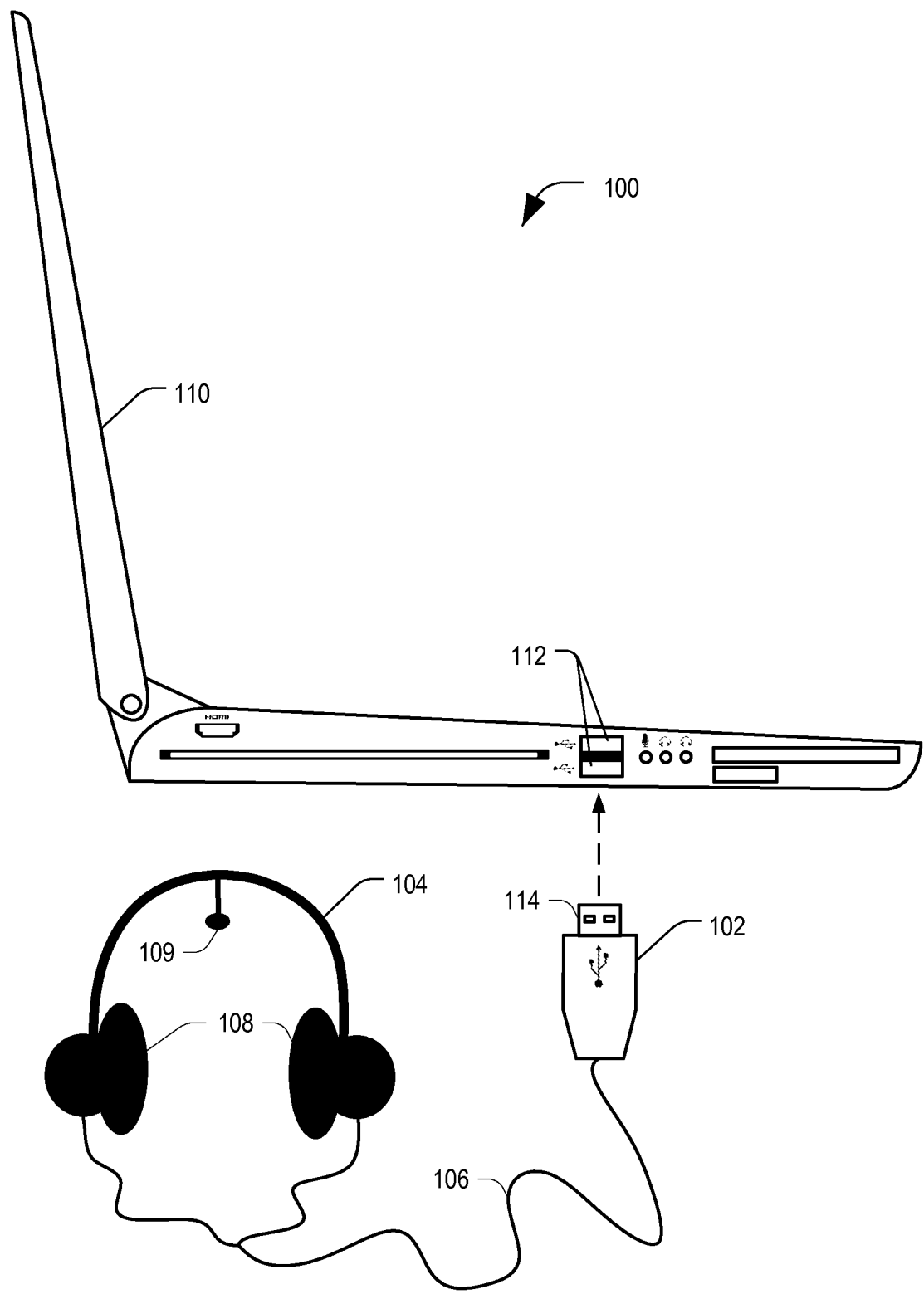
FIG. 1 is a pictorial view of an embodiment of a system including a portable tone generator for performing a hearing test.

FIG. 1 is a pictorial view of an embodiment of a system 100 including a portable tone generator 102 for performing a hearing test. System 100 includes a computing device 110 that has at least one input/output (I/O) port 112 for receiving a connector 122 of portable tone generator 102. Portable tone generator 102 is connected to a speaker system 104 via one or more wires 106. Speaker system 104 may include ahead set 108 including speakers, a bone conduction device 109, another known audio producing devices, or any combination thereof.

Portable tone generator 102 is a self contained device that is configured to be easily portable from one computing device 110 to another. The term portable as defined herein means "capable of being held in one hand". In particular one example, portable may mean a device that is similar in size to a cell phone, coffee cup, or television remote control. In another particular example, portable may be a device less than three inches long.

Computing device 110 may be a personal computer, a notebook computer, a phone (such as a smart phone), a tablet computer, a personal digital assistant (PDA), or another data processing device configurable to execute processor-readable instructions for performing a hearing test. Computing device 110 can send and receive a wide variety of signals to and from portable tone generator through I/O port 112. In some embodiments, computing device 110 controls operation of portable tone generator 102. In the illustrated embodiment, I/O port 112 is depicted as a universal serial bus (USB) port; however, I/O port 112 may be implemented with a variety of shapes and sizes and may be configured to utilize any of a variety of communication protocols.

Computing device 110 can be a general purpose data processing device including a processor, a memory, a display, and input interface (such as a keyboard, touch screen, track pad, or other input mechanism for receiving user input. The memory of computing device 110 can store instructions that, when executed by the processor, cause computing device to perform a variety of operations. In one example, such instructions, when executed, cause the processor to detect the portable tone generator 102 connected to the I/O port 112. In another example, upon detection of the portable tone generator 102, the processor retrieves instructions stored in a memory of the portable tone generator 102, including hearing test instructions, and automatically executes the instructions to generate a graphical user interface (GUI) for display on the display. The graphical user interface can include user instructions and user-selectable options for initiating and conducting a hearing test. Typically, the GUI includes at least one response input button that the user may select to initiate and/or pause the hearing test and at least one user-selectable element that the user may select to indicate that a tone was heard or a word was understood. The GUI may also display data indicating the progress of the hearing test.

In response to a user input related to a user-selectable option, button or element of the GUI, computing device can generate and provide control signals to portable tone generator 102. The control signals can include selected frequency information or other data suitable for instructing portable tone generator 102 to generate a sound and to provide the sound to speaker system 104, such as an audible tone or word. In a particular example, computing device 110 provides the control signals to portable tone generator 102, which control signal cause portable tone generator 102 to produce a sequence of tones or words for playback to the user via the speaker system 104. In a particular example, each control signal causes portable tone generator 102 to reproduce a tone that includes one or more selected frequencies and a specified amplitude for each of the selected frequencies. In another example, each control signal causes portable tone generator 102 to reproduce a part of speech or word that includes at least one selected speech part and a specified amplitude for each selected speech part. In some instances, the control signal may include duration or length of time during which portable tone generator 102 causes the tone to be reproduced by the speaker system 104.

Computing device 110 also includes additional instructions that, when executed by the processor, cause computing device 110 to provide the results of the hearing test to one of the display or another output port. In an example, the computing device 110 may include a port configurable to couple to a communications network, such as a public switched telephone network, a cellular network, and/or the Internet for communicating the results to a hearing health professional. In another example, computing device 110 may include a port, such as a printer port, a universal serial bus (USB) port, a network interface, or other port configured to communicatively couple to a printer for printing the results.

Portable tone generator 102 is coupled to speaker system 104 and configured to connect and communicate with computing device 110 through the I/O port 112. Portable tone generator 102 is shown with a male USB connector end 122, which connects to the I/O port 112 of computing device 110 to complete the connection. Portable tone generator 102 includes a controller configured to receive control signals from computing device 110 and coupled to tone generating circuitry to generate atone or word for the user at speaker system 104 in response to receiving the control signal. Portable tone generator 102 further includes a memory accessible by the controller for storing speaker system calibration measurements, frequency files, and speech files. Each frequency file includes data that can be processed by the controller to produce a signal for communication to the tone generating circuitry in conjunction with amplitude data to produce a tone. Each speech file includes a word or part of speech which is used by controller in combination or alone to test speech recognition. In some instances, the speaker calibration measurements may be incorporated into the frequency and speech files, such that the measurements do not have to be stored separately.

In operation, portable tone generator 102 is connected to computing device 104 though I/O port 112, allowing portable tone generator 102 to receive power and control signals from computing device 110. Computing device 110 executes instructions, which cause the GUI interface to be displayed by computing device 110 and a hearing test to begin. The GUI interface instructs the user to place speaker system 104 on his/her head, such that speaker system 104 covers the user's ear to provide isolation from ambient noise. In some instances, the GUI may also instruct the user to place the bone conduction device on his/her forehead, if a bone conduction system is incorporated into the speaker system 104.

Once the user is ready to begin a hearing test, computing device 110 executes the instructions, which cause computing device 110 to provide one or more control signals to portable tone generator 102. Portable tone generator 102 produces tones and provides them to the speaker system for reproduction by the speakers and/or bone conduction device in response to receiving the one or more control signals. In an example, the one or more control signals include data for producing a sequence of tones. Because portable tone generator 102 includes calibration measurements specific for speaker system 104, frequency and speech files, and its own controller, portable tone generator 102 may be used in conjunction with any computing device 110 to produce tones and/or speech with consistent, repeatable results. Moreover, portable tone generator 102 and associated speaker system 104 may be pre-calibrated to a level of accuracy sufficient to satisfy hearing aid testing requirements, making it possible to provide the portable tone generator 102 and speaker system 104 for use in connection with software to provide an at home hearing test.

White portable tone generator 102 produces tones and/or speech signals for reproduction by speaker system 104 for the user, computing device 110 displays a GUI including a button and instructions (text) to the user to select the button when the user hears a tone. Computing device 110 records responses made by the user and the timing of the responses (either at the correct time or at the incorrect time). Computing device 110 executes further instructions to analyze the responses received and, in response to the analysis, computing device 110 may vary the control signals provided to portable tone generator 102. By varying the control signals based on user responses, system 100 is able to generate a desired series of tones designed to pin point the user's individualized hearing loss and produce an audiogram, which is graphical representation of a person's auditory sensitivity to sound and which can be used by a hearing health professional to generate hearing profiles for configuring a hearing aid to compensate for the user's specific hearing impairment. In a particular example, system 100 may repeat specific control signals or a series of control signals causing portable tone generator 102 to reproduce the same tone or series of tones over again, such that computing device 110 is able to confirm that the user's response or failure to respond is the result of the user's hearing loss and not user error.

In the above-discussion, it is assumed that computing device 110 has instructions stored in a memory thereon that are executable by a processor to provide the GUI, to receive user selections, and to provide a hearing test. However, in an alternative embodiment, such instructions are stored in a memory of portable tone generator 102 and are provided to the processor for execution. In a particular embodiment, the instructions can include "auto run" instructions that cause the processor to automatically execute the instructions to perform the hearing test.

In the illustrated example, speaker system 104 is attached to portable tone generator 102 by wire 106. In this example, the wire 106 is permanently connected to portable tone generator 102. In an alternative embodiment, portable tone generator 102 may include a port for coupling to a connector, such as a tip-ring-sleeve type of connector (not shown), that is attached to wire 106.

FIG. 1 shows a pictorial view of system 100 to provide a context for the portable tone generator 102. An example of an embodiment of a portable tone generator 102 is described below with respect to FIG. 2.

Figure 2:
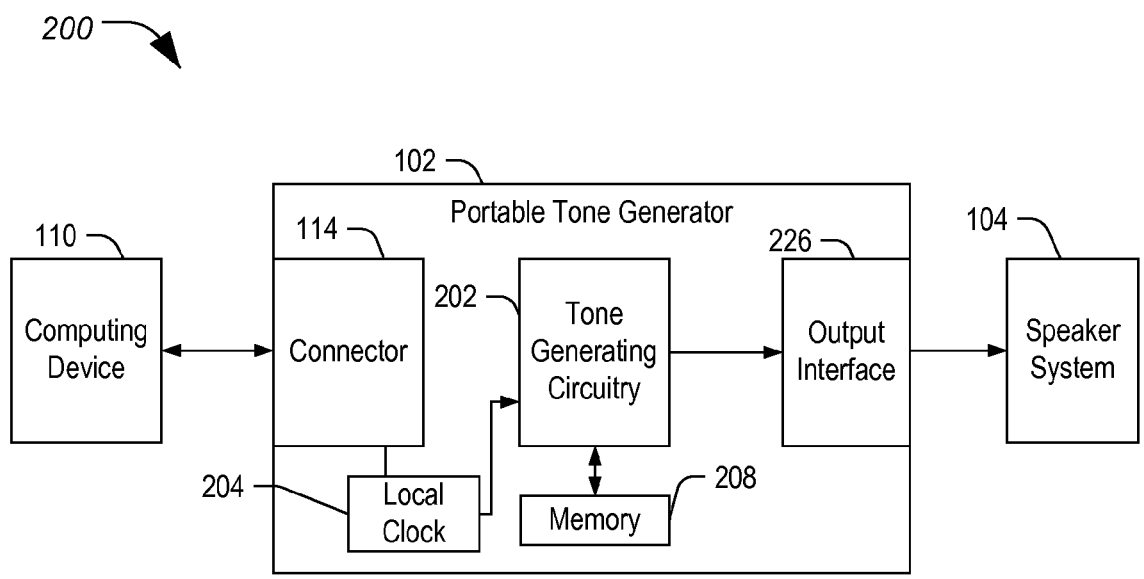
FIG. 2 is a block diagram of an embodiment of a system including a portable tone generator for performing a hearing test.

FIG. 2 is a block diagram of an embodiment of a system 200 including a portable tone generator 102 for performing a hearing test. Portable tone generator 102 includes a connector 206 configurable to connect to an input/output port 112 of a computing device 110. Portable tone generator 102 further includes tone generating circuitry 202 connected to connector 114, to memory 208, to local clock 204, and to output interface 226, which is connected to speaker system 104. Local clock 204 provides a calibrated clock signal that can be used by tone generating circuitry 202 to produce an audio signal having a desired frequency.

In an embodiment, tone generating circuitry 202 can be a digital signal processor. Alternatively tone generating circuitry 202 can include controller 306, digital gain amplifier 310, digital to analog converter 312, analog gain amplifier 322, and optionally filter 324 (depicted in FIG. 3). In still another embodiment, tone generating circuitry 202 can include a sound card configured to produce audio signals.

As opposed to a system that relies on the sound card and internal clock of computing device 110 to produce a tone, portable tone generator 102 is configured to operate with the same accuracy regardless of the computing device 110 connected to it. In one embodiment, portable tone generator 102 includes its own local clock 204 in addition to storing its own frequency files and speech files, which allow portable tone generator 102 to be calibrated for speaker system 104 independently of computing system 110. The independent calibration increases the portability of portable tone generator 102 and, opposed to other systems; portable tone generator 102 may operate with multiple computing devices 110 without requiring a re-calibration, resulting in a hearing test system which may be easily moved from one computing device 110 to another.

In a particular embodiment, portable tone generator 102 receives commands, instructions, and/or data from computing device 110 through connector 206. In response to such commands, instructions and/or data, portable tone generator 102 produces and provides at least one tone to speaker system 204 for audible reproduction for the user. Concurrently, computing device 110 may provide a graphical user interface including user-selectable options for responding to the at least one tone. Such responses and their timing relative to the tones can be recorded by computing device 110 and can be used to produce a hearing profile for the user.

Figure 3:
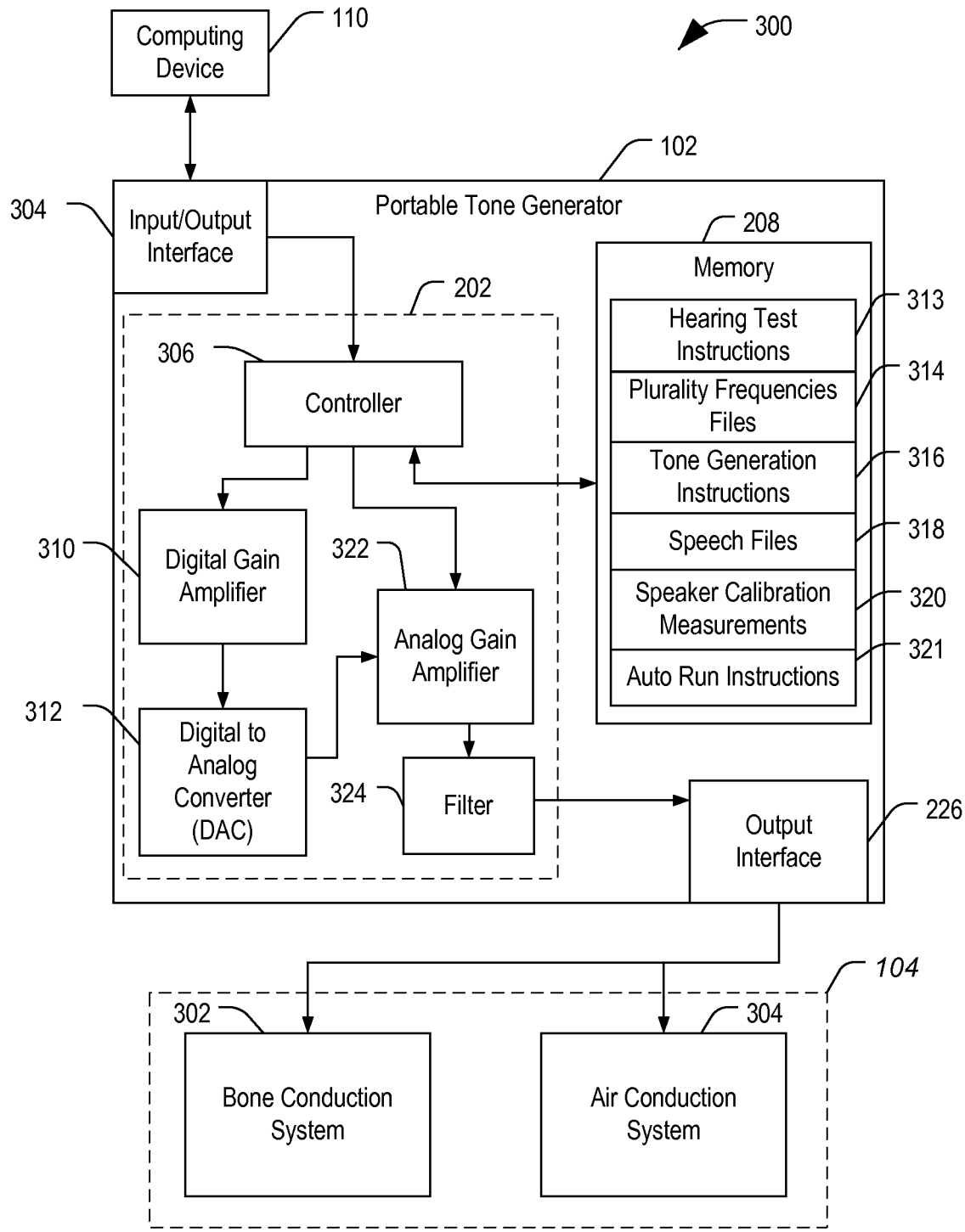
FIG. 3 is a block diagram of an second embodiment of a system including a portable tone generator for performing a hearing test.

FIG. 3 is a block diagram of a second embodiment of a system 300 for performing a hearing test. Portable tone generator 102 is connected to computing device 110 and to speaker system 104. Speaker system 104 may include a bone conduction system 302 and/or an air conduction system 303, such as head set 108. Portable tone generator 102 includes an input/output (I/O) interface 304, which communicatively couples to I/O port 112 of computing device 110 for receiving control signals. Portable tone generator 102 further includes an output interface 226 that couples to the speaker system 104 to provide an audio output signal (such as a tone or speech part), which is produced for the user as a sound or vibration.

Portable tone generator 102 includes tone generating circuitry 202. Tone generating circuitry 202 includes a controller 306 connected to I/O interface 304, which can include connector 114 (in FIG. 1). In some instances, controller 306 may be a digital signal processor configured to generate tones. Controller 306 has access to a memory 208. Memory 208 is configured to store speaker system calibration measurements 320, a plurality of frequency files 314, a plurality of speech files 318, and tone generating instructions 316. In some instances, memory 208 includes hearing test instructions 313 and auto-run instructions 321. Tone generating circuitry 202 also includes a digital gain amplifier 310 and an analog gain amplifier 322 coupled to controller 306 and configured to adjust the amplitude of the audio output signal.

Tone generating circuitry 202 also includes a digital to analog converter (DAC) 312 having an input connected to an output of the digital gain amplifier 310 and an output connected to an input of analog gain amplifier 322. Analog gain amplifier 322 includes an output connected to an input of a filter 324, which has an output connected to an input of output interface 226. In some instances, filter 324 may be omitted, such as when the audio output signal from analog gain amplifier 322 is free from distortions.

In an example, portable tone generator 102 receives a control signal or a series of control signals from computing device 110 at I/O interface 304. As described above, each control signal includes an identified frequency or speech part, an amplitude, and a duration. Controller 306 receives the control signal from I/O interface 304 and executes tone generation instructions 316 in response thereto. The tone generating instructions 316 cause controller 306 to retrieve a frequency file and/or a speech file from the plurality of frequencies files 314 or the plurality of speech files 318, respectively, and to provide an audio signal to the input of digital gain amplifier 310 based on the retrieved data.

Tone generating instructions 316 also cause controller 306 to access the speaker calibration measurements 320 and to generate a first and second amplitude control signals based on the speaker calibration measurements 320 and optionally based on amplitude instructions included within the control signal. Controller 306 provides the first amplitude control signal to the digital gain amplifier 310 and the second amplitude control signal to the analog gain amplifier 322.

Digital gain amplifier 310 sots an initial amplitude of the audio output signal in response to receiving the first amplitude control signal. For example, digital gain amplifier 310 applies a gain to the audio output signal to set the amplitude to an initial value based on the first amplitude control signal. In an example, digital gain amplifier 310 has a gain that can be programmed incrementally, such as increments of 4 db, 8 db, 12 db, and so forth. Once the initial amplitude is set by digital gain amplifier 310, digital gain amplifier amplifies the audio output signal and provides the amplified audio output signal to DAC 312, which converts it to an analog signal and provides the analog output signal to analog gain amplifier 322. Analog gain amplifier 322 further refines the amplitude of the analog output signal in response to receiving the second amplitude control signal from controller 306. For example, if digital gain amplifier 310 adjusts the amplitude in increments of 4 dB as described above, analog gain amplifier 310 can adjust the amplitude by smaller increments, such as 0, 1, 2, or 3 dBs. Thus, if the first control signal instructed digital gain amplifier 310 to adjust the amplitude by 4 dB and the second amplitude control signal instructs analog gain amplifier 322 to adjust the amplitude by 1 dB, after being adjusted by both digital and analog gain amplifiers 310 and 322, the analog output signal would have a resulting gain of 5 dB. Digital and analog gain amplifiers 310 and 322 can also be used to provide other sizes of incremental gains. In this manner, the audio output signal may be gain-adjusted to any decibel level within the human hearing range.

The audio output signal is provided to filter 324 after the amplitude is adjusted by the digital gain amplifier 310 and the analog gain amplifier 322. Filter 324 removes any anomalies or disturbances from the audio output signal by smoothing the audio output signal before providing it to output interface 226 for reproduction by speaker system 104.

In an example, the portable tone generator 102 selectively configures a set of frequency curve values representative of a desired sound to produce a part of speech or a tone as designated by a control signal from computing device 110 to generate an audio output signal. Portable tone generator 102 can select a tone or speech file from a plurality of tone and speech files stored in memory 208 on the portable tone generator 102 to match the part of speech or tone designated by the control signal.

Portable tone generator 102 is self-contained with stored frequency, speech, tone, and speaker calibration files 314, 318, 316, and 320, respectively, and optionally with hearing test instructions 313 and auto run instructions 321. Thus, portable tone generator 102 may be used with a wide range of computing devices having different types of hardware while still being capable of providing the calibrated tones. Further, different versions of the software may be provided or a cross-platform application may be used that can be executed within various operating systems. In particular, portable tone generator 102 can be used with any computing device 110 that has hardware suitable for connecting to portable tone generator 102 and for executing various hearing test software. Therefore, portable tone generator 102 produces a hearing test that maintains accuracy and produces precise test results independent of which computing device 110 is used. Further, portable tone generator 102 may be calibrated to industry standards independent of the computing device to meet state and/or federal mandated calibration requirements for human hearing tests. Thus, system 300 can be used to provide an at home hearing test that can meet the industry standards for accurate hearing evaluation test results.

In another example, tone generating circuitry (such as tone generating circuitry 202 in FIG. 2) is coupled to an input interface (such as connector 114) and to a memory 208 that stores data related to a tone or frequency. In response to receiving control signals from computing device 110, tone generating circuitry 202 retrieve the data from the memory and generates an output signal based on the data. Tone generating circuitry 202 provides the output signal to output interface 226 for providing the output signal to a speaker system 104.

Speaker system 104 may reproduce the output signal using bone conduction system 302, air conduction system 304, or a combination of the two. In a first example, speaker system 104 reproduces the output signal as sound using air conduction system 204. The output signal may be reproduced at a user's left ear, right ear, or both ears. In a second example speaker system 104 reproduces the output signal as a vibration using bone conduction system 302. Bone conduction system 302 works by producing a vibration at the frequency of the tone at a vibrator which is typically attached to a patient's forehead. The patient's inner ear is able to detect the vibrations, such that the user hears the tone. Because the vibrations cannot be applied to only a right or left ear, speaker system 104 may also produce a masking signal at the non-test ear to cancel or drown out the tone produced by the vibration. The masking signal is produced using air conduction system 304 at the non-test ear and typically includes producing a large amount of white noise in a frequency band around the frequency of the tone, thus drowning out the tone at that ear.

In an example, portable tone generator 102 can be implemented as a USB thumb drive with audio processing capabilities and an audio output to speaker system 104. As previously mentioned, speaker system 104 may be permanently attached to portable tone generator 102 or releasably attached, such as by using a tip-ring-sleeve connector. Alternatively, portable tone generator 102 can be configured as an external component that can couple to a computing device via an I/O port 112, such as a USB port, and that controls the headset 108 to produce the desired tones and/or other audio output. While FIG. 3 depicts system 300 for providing a hearing test utilizing portable tone generator 102, FIG. 4 shows a method for providing the hearing test.

As opposed to a calibration system which monitors and analyzes tone signals (analog sound signals) and performs a calibration on the tone signal based on the analysis, portable tone generator 102 receives control signals from computing device 110 instead and is able to generate a calibrated tone from the control signals and stored plurality of frequencies files 314 without any monitoring or analyzing. Thus the audio monitoring and analyzing components of calibration systems are not required to produce portable tone generator 102 allowing portable tone generator 102 to be smaller and less expensive.

Figure 4:
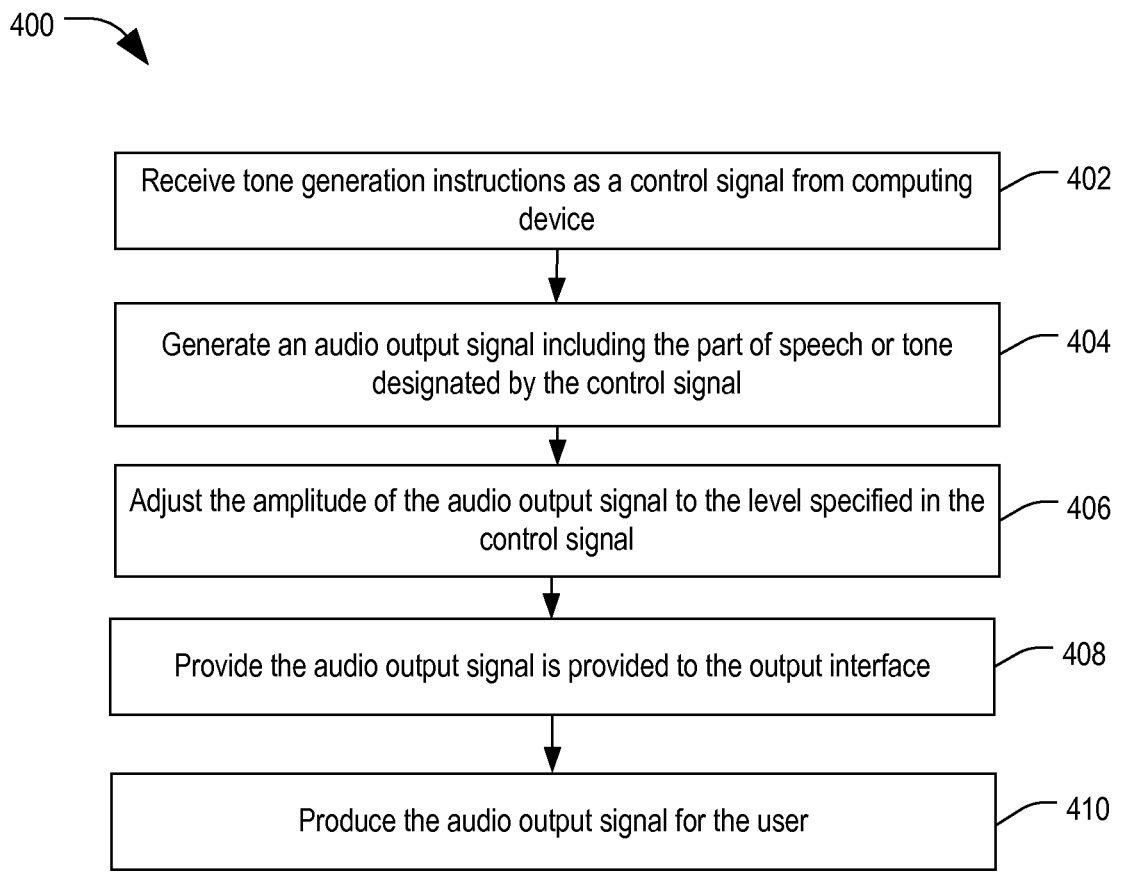
FIG. 4 is a flow diagram of an embodiment of a method of performing a hearing test using a portable tone generator.

FIG. 4 is a flow diagram of an embodiment of a method 400 of performing a hearing test using a portable tone generator. At 402, the portable tone generator receives tone generation instructions via a control signal from a computing device. In an embodiment, the control signal includes an identifier for a part of speech or a tone to produce as sound and a specified amplitude for each identified part of speech or tone. While the control signal identifies a part of speech or tone to produce at sound, it does not necessarily include the speech or tone files, which can be stored locally on the portable tone generator 102. In an alternative embodiment, the control signal includes a sequence that corresponds to particular frequencies, tones, or other parts of speech, which can be retrieved and generated by the portable tone generator 102 in response to the control signals.

Proceeding to 404, the portable tone generator generates an audio output signal including the part of speech or tone designated by the control signal. In one particular example, portable tone generator selectively configures a set of frequency curve values representative of a desired sound to produce the part of speech or tone as designated by the control signal to generate the audio output signal. Typically, the portable tone generator selects a tone or speech file from a plurality of tone and speech files stored in memory on the portable tone generator to match the part of speech or tone designated by the control signal. Advancing to 406, the portable tone generator adjusts the amplitude of the audio output signal to the level specified in the control signal. The portable tone generator is able to access stored speech calibration information when adjusting the amplitude of the audio output signal to ensure accurate test results, and may also filter the audio output signal after the amplitude has been adjusted to smooth the audio output signal. Continuing to 408, the audio output signal is provided to the output interface, which is coupled to a speaker or bone conduction device. Proceeding to 410, the speaker or bone conduction device produces the audio output signal for the user.

In an example, portable tone generator 102 can be used in conjunction with hearing test software configured to provide a graphical user interface to guide or prompt a user through a hearing test. The hearing test software may be provided in a memory of portable tone generator 102. Alternatively, the hearing test software may be provided on a compact disc, a portable memory device (such as a USB "thumb" drive), and/or on a server accessible via a network such as the Internet. Portable tone generator 102 can be used with proprietary or open source software. By providing a portable tone generator 102 with built-in, calibrated, tone generating circuitry 202 and a known speaker system 104, the portable tone generator 102 can be used with any type of computing device to provide a calibrated, reliable hearing test with accurate, reliable, and reproducible sound quality that satisfies state and federal requirements.

In conjunction with the systems, circuits, and methods described above with respect to FIGS. 1-4, a portable tone generator is disclosed that includes an input/output interface configurable to connect to an input/output port of a computing device, an output interface connected to a headset including at least one of a speaker system and a bone conduction system, and a tone generator coupled to the input/output interface and to the output interface, the tone generator configured to generate one or more tones in connection with a hearing test.

Although the present invention has been described with reference to preferred embodiments, workers skilled in the art will recognize that changes may be made in form and detail without departing from the scope of the invention.

What is claimed is:

1. A portable tone generator comprising:
   a connector configurable to couple to an input/output port of a computing device;
   a speaker system integrated with the portable tone generator;
   a memory, internal to the portable tone generator, configured to store calibration data related to the speaker system; and
   tone generating circuitry, internal to the portable tone generator, configured to receive a control signal from the computing device, the control signal to cause the speaker system to output a tone at a selected amplitude and in response to receiving the control signal to adjust the amplitude indicated in the control signal based at least in part on the calibration data related to the speaker system before the tone is output by the speaker system.

2. The portable tone generator of claim 1, wherein the speaker system comprises an air conduction device configured to provide sound into an ear of a user.

3. The portable tone generator of claim 1, wherein the speaker system comprises a bone conduction device configured to couple sound into an ear of a user through ear bones of the ear.

4. The portable tone generator of claim 1, wherein the speaker system comprises at least one ear phone including a speaker for reproducing the tone.

5. The portable tone generator of claim 1, wherein the connector comprises a universal serial bus (USB) connector.

6. The portable tone generator of claim 1, wherein the control signal includes a selected frequency.

7. The portable tone generator of claim 1, wherein calibration data includes pre-calibrated tones.

8. The portable tone generator of claim 1, wherein calibration data includes sound characteristics of the speaker system.

9. A portable tone generator comprising:
   a memory configured to store data related to a hearing test;
   an input interface configurable to couple to a computing device for receiving a control signal;
   an output interface coupled to the tone generating circuitry for providing the output signal to a speaker system; and
   tone generating circuitry coupled to the input interface and the memory, the tone generating circuitry comprising:
      a digital gain amplifier configured to apply a first adjustment to a tone signal in response to receiving a first amplitude control signal;
      an digital-to-analog converter coupled to the digital gain amplifier for converting the tone signal into an analog format;
      an analog gain amplifier coupled to the digital-to-analog converter and the output interface converter and configured to apply a second adjustment to the tone signal in response to receiving a second amplitude control signal;
      a controller coupled to the input interface, the memory, the digital gain amplifier, and the analog gain amplifier and configured to receive the instructions and, in response to receiving the instructions, the controller is configured to:
         select a frequency from memory;
         generate a tone signal based on the frequency;
         generate a first amplitude control signal and provide the first amplitude control signal to the digital gain amplifier;
         generate a second amplitude control signal and provide the second amplitude control signal to the analog gain amplifier; and provide the tone signal to the digital gain amplifier; and
      wherein the output interface receives the tone signal from the analog gain amplifier and provides the tone signal to the speaker system as the output signal.

10. The portable tone generator of claim 9, wherein the data related to a hearing test includes data related to a plurality of frequencies.

11. The portable tone generator of claim 9, wherein the data related to a hearing test includes data related to a plurality of speech parts.

12. The portable tone generator of claim 11, wherein output signal comprises a sound signal including a part of speech.

13. The portable tone generator of claim 9, wherein the input interface comprises a Universal Serial Bus (USB) connector configured to couple to a USB port of the computing device.

14. The portable tone generator of claim 9, wherein the input interface is configured to receive power and data from the computing device.

15. The portable tone generator of claim 9, wherein the tone generating circuitry comprises a digital signal processor for producing the output signal.

16. The portable tone generator of claim 9, wherein the memory stores data related to the plurality of frequencies calibrated for the speaker-system.

17. A method comprising:
   receiving a control signal indicating a frequency and amplitude from a computing device at a portable tone generator coupled to the computing device, the portable tone generator including an internal memory to store data related to production of one or more pre-calibrated tones and an integrated speaker system, the pre-calibrate tones tuned to compensate for the sound characteristics of the integrated speaker system;
   retrieving a pre-calibrated tone from the internal memory based at least in part on the frequency and amplitude indicated in the control signal;
   outputting the pre-calibrated tone.

18. The method of claim 17, wherein the speaker system comprises an air conduction device configured to provide sound into an ear of a user.

19. The method of claim 17, wherein the speaker system comprises a bone conduction device configured to couple sound into an ear of a user through ear bones of the ear.

20. The method of claim 17, wherein the speaker system comprises at least one ear phone including a speaker for reproducing the tone.

* * * * *